July 16, 1957 H. L. CORCORRAN Plant Pat. 1,622
ALMOND TREE
Filed Oct. 16, 1956
Fig. 1
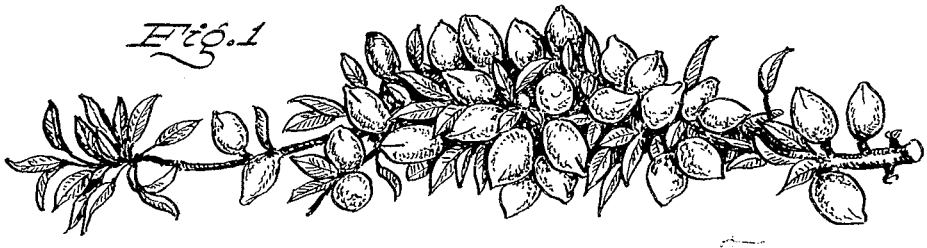
Fig. 2
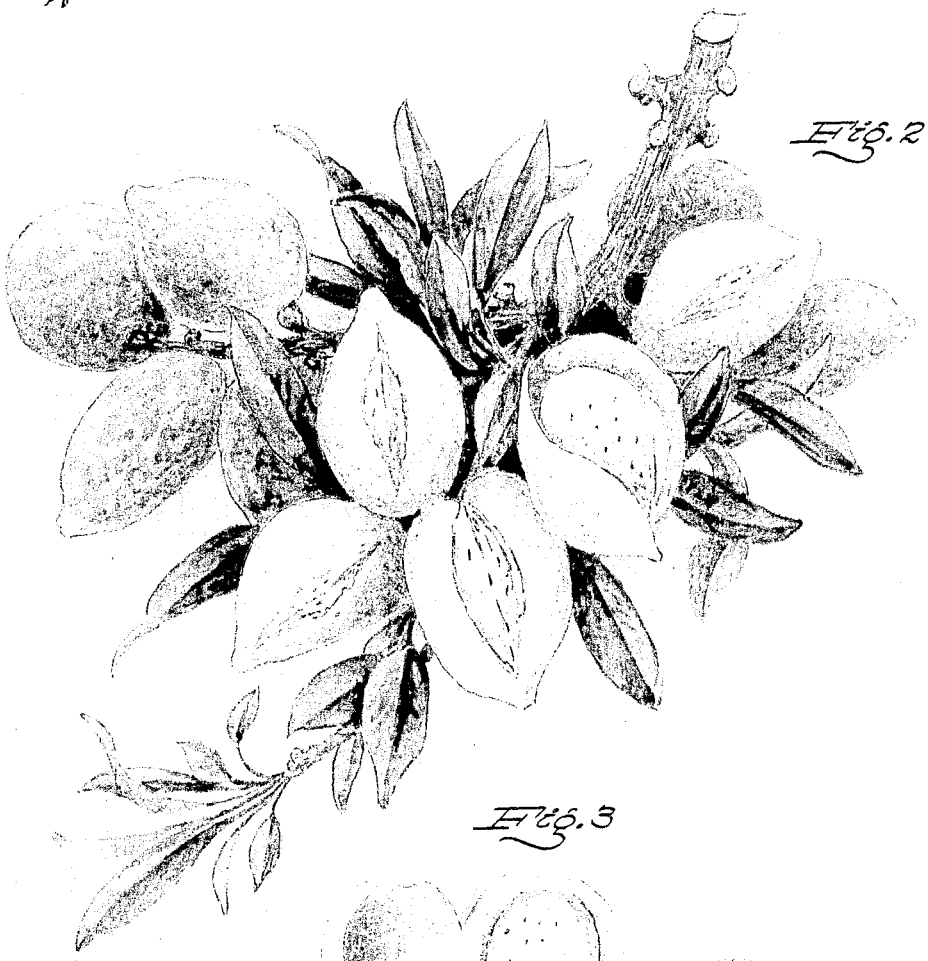
Fig. 3
Fig. 4
Fig. 5
WITNESS
Addison E. Avery
INVENTOR
Herbert Lee Corcorran
Webster & Webster
ATTYS.

United States Patent Office

Plant Pat. 1,622
Patented July 16, 1957

1,622

ALMOND TREE

Herbert Lee Corcorran, Delhi, Calif.

Application October 16, 1956, Serial No. 616,360

1 Claim. (Cl. 47—62)

This invention relates to a new and distinct variety of almond tree which was originated by me on my ranch near Delhi, California; the seed parent having been a Nonpareil almond, while the pollen parent is not positively known, as I was experimenting with pollen from the Jordanolo, Ne Plus Ultra, and Texas almonds, and the Santa Rosa plum, and under conditions of possible open-pollination.

A seed of the cross produced the present variety, and which—has a seedling—was observed to have an especially fast and vigorous growing habit. Planted in my orchard, this seedling—when it subsequently came into maturity—was found to bear, in profusion, a very commercially desirable nut.

I therefore selected the variety for asexual reproduction, and this was accomplished on my ranch—located as aforesaid—by grafting, as well as by budding, onto mature orchard trees. These reproductions were found to carry forward the characteristics of the parent tree in full.

The present almond variety is particularly characterized by a large, dense tree which is fast and vigorous in growth, and thus easy to shape by pruning.

Further, the tree blooms heavily (possibly a pollinizer for the Nonpareil), and such blooming occurs at approximately the same time as said Nonpareil.

Additionally, the present variety sets and bears the nuts in great profusion, and with the nuts well distributed along the branches. While the present variety blooms approximately with the Nonpareil, it harvests about one week later.

The nuts, while hanging well on the tree, are easy to harvest and hull; such nuts being of medium soft-shell type. The shell is a golden straw color, well sealed, and has a wing or flange along the ventral edge which snaps out readily when twisted with the fingers, which is a substantial aid to manual shelling. The meats—which are slightly darker in skin color than the Nonpareil—are good, and sweet.

In the original drawings:

Fig. 1 is an elevation of substantially a full branch showing the profusion and distribution of the nuts thereon.

Fig. 2 is an enlarged fragmentary elevation of a branch showing the nuts and leaves; certain of the hulls being shown partly open.

Fig. 3 is an elevation of one of the nuts with the hull full-open and exposing the shell.

Fig. 4 is an elevation showing one of the kernels in a half-shell.

Fig. 5 is a similar view, but shows the kernel as cut to expose the meat.

Referring now more specifically to the botanical details of this new and distinct variety of almond tree, the following is an outline description thereof; all major color plate identifications being by reference to Maerz and Paul Dictionary of Color:

Tree:
- *Density.*—Dense.
- *Size.*—Large.
- *Vigor.*—Vigorous.
- *Branching habit.*—Medium.
- *Color of bark.*—Reddish brown.
- *Foliage.*—Abundant. Leaves: Size—medium; average length, 2¼″; average width, ¾″. Shape—wide, lanceolate. Margin—crenate. Color—top side, medium green (21–L–6); under side, slightly lighter green (21–J–6). Bloom: Amount of bloom—very heavy. Color—white, flushed with pink. Blooming period—blooms approximately with the Nonpareil almond.

Crop:
- *Productivity.*—Very heavy.
- *Distribution of nuts on tree.*—Well distributed.
- *Harvest period.*—About one week after the Nonpareil almond.
- *Tenacity.*—Hangs well on the tree; easy to harvest; easy to hull.

Hull: Smooth; regular; medium thick.
- *Suture.*—Flat; lightly ridged.
- *Dehiscence.*—Opens freely. Splitting—along suture.
- *Color.*—Before full ripe—olive grey (13–A–1 to 15–C–1). When ripe—at the time of opening—light grey with olive sheen (11–J–3 to 13–J–4).

Nut:
- *Size.*—Average length, 1⅜″. Average width, 15/16″. Average thickness, ¾″. Average weight—largest nuts count 18/20 per ounce; smallest nuts count 23/25 per ounce.
- *Form.*—Length/width—ovate. Width/thickness—plump or medium.
- *Shell.*—Medium soft. Outer shell—bony; inner shell—well sealed.
- *Pits.*—Large.
- *Base.*—Square. Stem scar—small.
- *Apex.*—Medium sharp.
- *Wing.*—Medium narrow. The wing or flange—which serves as an effective seal strip—readily snaps out for ease of opening. Inner surface—medium. Ventral streak—medium broad; long.
- *Percentage of kernel to nut.*—Average crack-out, 48%.
- *Color.*—Golden straw (9–E–3).

Kernel:
- *Size.*—Average length, 1 1/16″; average width, 9/16″; average thickness, 5/16″.
- *Form.*—Length/width—ovate. Width/thickness—medium.
- *Base.*—Square. Stem scar—small.
- *Apex.*—Obtuse.
- *Plumpness.*—Lightly wrinkled.
- *Pellicle.*—Thin.
- *Number of doubles.*—Very few.
- *Flavor.*—Sweet; oily.
- *Quality.*—Good.
- *Color of skin.*—Light brown (10–L–11).
- *Color of meat.*—White (9–A–1), with a pale ivory cast.

The tree and its nuts herein described may vary in slight detail due to climatic and soil conditions under which the variety may be grown.

As far as is known to me, the prior varieties—identified in the foregoing specification—are unpatented.

The following is claimed:

A new and distinct variety of almond tree, as shown and described, characterized by the tree being large, dense, and fast and vigorous in growth; by blooming heavily and approximately with the Nonpareil; by setting and bearing the nuts in great profusion and well distributed along the branches; by nuts which hang well on the tree, and are easy to harvest and hull; by harvesting about one week later than the Nonpareil; by medium soft-shell nuts whose shell is a golden straw color, well sealed, and having a wing which snaps out readily; and by good, sweet meats whose skin color is slightly darker than said Nonpareil.

No references cited.